(12) United States Patent
Price

(10) Patent No.: US 9,211,284 B2
(45) Date of Patent: Dec. 15, 2015

(54) DIAGNOSIS AND TREATMENT OF P.R.I.C.E. SYNDROME

(71) Applicant: Richard Louis Price, Suffern, NY (US)

(72) Inventor: Richard Louis Price, Suffern, NY (US)

( * ) Notice: Subject to any disclaimer, the term of this patent is extended or adjusted under 35 U.S.C. 154(b) by 246 days.

(21) Appl. No.: 13/860,824

(22) Filed: Apr. 11, 2013

(65) Prior Publication Data

US 2014/0309269 A1 Oct. 16, 2014

(51) Int. Cl.
*A61K 31/4168* (2006.01)
*A61K 31/047* (2006.01)
*A61K 31/165* (2006.01)

(52) U.S. Cl.
CPC ............ *A61K 31/4168* (2013.01); *A61K 31/047* (2013.01); *A61K 31/165* (2013.01)

(58) Field of Classification Search
USPC .................................................. 514/401, 617
See application file for complete search history.

(56) References Cited

U.S. PATENT DOCUMENTS

| 3,454,701 A | 7/1969 | Zeile et al. |
| 5,854,290 A | 12/1998 | Arnsten et al. |
| 5,869,100 A | 2/1999 | Horacek |
| 6,287,599 B1 | 9/2001 | Burnside et al. |
| 6,811,794 B2 | 11/2004 | Burnside et al. |
| 8,062,667 B2 | 11/2011 | Mehta et al. |
| 8,287,903 B2 | 10/2012 | Mehta et al. |
| 8,455,548 B2 | 6/2013 | Luhrs et al. |
| 8,557,792 B2 | 10/2013 | Castelli et al. |

OTHER PUBLICATIONS

Yale University, Guanfacine for the Treatment of Hyperactivity in Pervasive Developmental Disorder, https://clinicaltrials.gov/ct2/show/study!NCTO 1238575?term=intuniv+hyperactivity+in+au; Aug. 19, 2014.
J. Levine, et al., Inositol treatment of autism, J Neural Transm (1997) 104: 307-310.
K., Blankenship, et al., Guanfacine Extended Release in Two Patients with Pervasive Developmental Disorders, Journal of Child and Adolescent Psychopharmacology, vol. 21, No. 3, 2011, pp. 287-290.
X., Ming, et al., Use of clonidine in children with autism spectrum disorders, Brain & Development 30 (2008) 454-460.
International Search Report and Written Opinion for PCT Patent Application PCT/US2014/032933 dated Aug. 7, 2014.

*Primary Examiner* — Kathrien Cruz
(74) *Attorney, Agent, or Firm* — David B. Gornish

(57) ABSTRACT

A method for treating a patient having P.R.I.C.E. Syndrome is disclosed. The method includes administering to the patient a therapeutically effective amount of an alpha-2 adrenergic agonist in an extended release dosage form.

18 Claims, No Drawings

DIAGNOSIS AND TREATMENT OF P.R.I.C.E. SYNDROME

BACKGROUND OF THE INVENTION

1. Field of Invention

The invention relates to diagnosis and treatment of a psychiatric disorder defined herein as P.R.I.C.E. Syndrome. More particularly, the invention relates to administering to a person having P.R.I.C.E. Syndrome an extended release composition of a therapeutically effective amount of an alpha-2 adrenergic agonist, such as clonidine or guanfacine.

2. Description of Related Art

When a psychiatrist is presented with a patient exhibiting one or more behaviors such as poor social skills, defiance, lack of patience, difficulty paying attention, ritualistic behavior and/or mood swings, where such behavior(s) interferes with normal functioning, the psychiatrist must first make a diagnosis before formulating a treatment plan. A patient having dysfunctional levels of any/some/all of the foregoing symptoms may, depending on the psychiatrist's professional judgment, be determined to have any of the following conditions: Pervasive Developmental Disorder ("PDD") or Autistic Spectrum Disorder ("ASD") such as Autistic Disorder, Asperger's Disorder, Rett's Disorder, Childhood Disintegrative Disorder, Schizophrenia or other Psychotic Disorder, Attention Deficit Hyperactivity Disorder ("ADHD"), Obsessive Compulsive Disorder ("OCD"), Hypomania in Bipolar Disorder, Intermittent Explosive Disorder, an Impulse Control Disorder, or a Personality Disorder.

Today, the psychiatrist's nomenclature, i.e., the criteria for psychiatric evaluation and classification is provided in the DSM-IV-TR (the "Diagostic and Statistical Manual of Mental Disorders"), a periodically revised psychiatric "Bible" published by the American Psychiatric Association. The next revision of the DSM, the DSM-V, is currently scheduled to be published in late 2013.

The psychiatrist's professional judgment in rendering a diagnosis is largely informed by the criteria for various disorders set forth in the DSM. Thus, a psychiatrist presented with a patient exhibiting any such symptoms as those described above would consult the DSM in rendering a diagnosis. The diagnosis would, in turn, inform a treatment program. Whether a given patient is determined, for example, to have ADHD as opposed to Asperger's Disorder or Hypomania in Bipolar Disorder, depends on whether the patient's symptoms comport with criteria set forth for these conditions in the DSM. Proper diagnosis is critical since a wrong diagnosis will likely lead to an ineffective or even potentially harmful treatment program.

The DSM-IV-TR classifications for the disorders discussed above are as follows:

Autistic Disorder, DSM-IV-TR 299.00

Autistic Disorder, according to the DSM-IV-TR is defined as:
A. A total of six or more items from (1), (2), and (3), with at least two for (1), and one each from (2) and (3):
 (1) Qualitative impairment in social interaction, as manifested by at least two of the following:
 (a) marked impairment in the use of multiple nonverbal behavior such as eye-to-eye gaze, facial expression, body postures, and gestures to regulate social interaction
 (b) failure to develop peer relationships appropriate to developmental level
 (c) a lack of spontaneous seeking to share enjoyment, interests, or achievements with other people (e.g., by a lack of showing, bringing, or pointing out objects of interest)
 (d) lack of social or emotional reciprocity
 (2) Qualitative impairments in communication as manifested by at least one of the following:
 (a) delay in, or total lack of, the development of spoken language (not accompanied by an attempt to compensate through alternative modes of communication such as gesture or mime)
 (b) in individuals with adequate speech, marked impairment in the ability to initiate or sustain a conversation with others
 (c) stereotyped and repetitive use of language or idiosyncratic language
 (d) lack of varied, spontaneous make-believe play or social imitative play appropriate to developmental level
 (3) Restricted repetitive and stereotyped patterns of behavior, interests, and activities, as manifested by at least one of the following:
 (a) Encompassing preoccupation with one or more stereotyped and restricted patterns of interest that is abnormal either in intensity or focus
 (b) Apparently inflexible adherence to specific, nonfunctional routines and rituals
 (c) Stereotyped and repetitive motor mannerisms (e.g., hand or finger flapping or twisting, or complex whole body movements
 (d) Persistent preoccupation with parts of objects
B. Delays or abnormal functioning in at least one of the following areas, with onset prior to age 3 years: (1) social interaction, (2) language as used in social communication, or (3) symbolic or imaginative play.
C. The disturbance is not better accounted for by Rett's Disorder or Childhood Disintegrative Disorder.

Rett's Disorder, DSM-IV-TR 299.80

Rett's Disorder, according to the DSM-IV-TR is defined as:
A. All of the following:
 (1) Apparently normal prenatal and perinatal development
 (2) Apparently normal psychomotor development through the first 5 months after birth
 (3) Normal head circumference at birth
B. Onset of all of the following after the period of normal development:
 (1) Deceleration of head growth between age 5 and 48 months
 (2) Loss of previously acquired purposeful hand skills between ages 5 and 30 months with the subsequent development of stereotyped hand movements (e.g., hand-wringing or hand washing)
 (3) Loss of social engagement early in the course (although often social interaction develops later)
 (4) Appearance of poorly coordinated gait or trunk movements
 (5) Severely impaired expressive and receptive language development with severe psychomotor retardation.

Childhood Disintegrative Disorder, DSM-IV-TR 299.10

Childhood Disintegrative Disorder, according to the DSM-IV-TR is defined as:
A. Apparently normal development for at least the first 2 years after birth as manifested by the presence of age-appropriate verbal and nonverbal communication, social relationships, play, and adaptive behavior.

B. Clinically significant loss of previously acquired skills (before age 10 years) in at least two of the following areas:
(1) Expressive or receptive language
(2) Social skills or adaptive behavior
(3) Bowel or bladder control
(4) Play
(5) Motor skills C. Abnormalities of functioning in at least two of the following areas:
(1) Qualitative impairment in social interaction (e.g., impairment in nonverbal behaviors, failure to develop peer relationships, lack of social or emotional reciprocity)
(2) Qualitative impairments in communication (e.g. delay or lack of spoken language, inability to initiate or sustain a conversation, stereotyped and repetitive use of language, lack of varied make-believe play)
(3) Restricted, repetitive, and stereotyped patterns of behavior, interests, and activities, including motor stereotypes and mannerism D. The disturbance is not better accounted for by another specific Pervasive Developmental Disorder or by Schizophrenia.

Asperger's Disorder, DSM-IV-TR 299.80

Asperger's Disorder, according to the DSM-IV-TR is defined as:
A. Qualitative impairment in social interaction, as manifested by at least two of the following:
(1) Marked impairment in the use of multiple nonverbal behavior such as eye-to-eye gaze, facial expression, body postures, and gestures to regulate social interaction
(2) Failure to develop peer relationships appropriate to developmental level
(3) A lack of spontaneous seeking to share enjoyment, interests, or achievements with other people (e.g., by a lack of showing, bringing, or pointing out objects of interest to other people)
(4) Lack of social or emotional reciprocity B. Restricted repetitive and stereotyped patterns of behavior, interests, and activities, as manifested by at least one of the following:
(1) Encompassing preoccupation with one or more stereotyped and restricted patterns of interest that is abnormal either in intensity or focus
(2) Apparently inflexible adherence to specific, nonfunctional routine or rituals
(3) Stereotyped and repetitive motor mannerisms (e.g., hand or finger flapping or twisting, or complex whole-body movements)
(4) Persistent preoccupation with parts of objects C. The disturbance causes clinically significant impairment in social, occupational, or other important area of functioning.

D. There is no clinically significant general delay in language (e.g., single words used by age 2 years, communicative phrases used by age 3 years).

E. There is no clinically significant delay in cognitive development or in the development of age-appropriate self-help skills, adaptive behavior (other than in social interaction), and curiosity about the environment in childhood.

F. Criteria are not met for another specific Pervasive Developmental Disorder or Schizophrenia.

Pervasive Development Disorder not Otherwise Specified (Including Atypical Autism), DSM-IV-TR 299.80

Pervasive Development Disorder Not Otherwise Specified (Including Atypical Autism), according to the DSM-IV-TR is defined as:
This category should be used when there is a severe and pervasive impairment in the development of reciprocal social interaction associated with impairment in either verbal or nonverbal communication skills or with presence of stereotyped behavior, interests, and activities, but the criteria are not met for a specific Pervasive Developmental Disorder, Schizophrenia, Schizotypal Personality Disorder, or Avoidant Personality Disorder. For example, this category includes "atypical autism"—presentations that do not meet the criteria for Autistic Disorder because of late age of onset, atypical symptomatology, or sub-threshold symptomatology, or all of these.

Attention-Deficit/Hyperactivity Disorder, DSM-IV-TR 314.01, 314.00

Attention-Deficit/Hyperactivity Disorder, according to the DSM-IV-TR is defined as:
A. Either (1) or (2):
(1) Six (or more) of the following symptoms of inattention have persisted for at least 6 months to a degree that is maladaptive and inconsistent with development level:
Inattention
(a) Often fails to give close attention to details or makes careless mistakes in schoolwork, work, or other activities
(b) Often has difficulty sustaining attention in tasks or play
(c) Often does not seem to listen when spoke to directly
(d) Often does not follow through on instructions and fails to finish schoolwork, chores, or duties in the workplace (not due to oppositional behavior or failure to understand instructions)
(e) Often has difficulty organizing tasks and activities
(f) Often avoids, dislikes, or is reluctant to engage in tasks that require sustained mental effort (such as schoolwork or homework)
(g) Often loses things necessary for tasks or activities (e.g., toys, school assignments, pencils, books, or tools)
(h) Is often easily distracted by extraneous stimuli
(i) Is often forgetful in daily activities
(2) Six (or more) of the following symptoms of hyperactivity-impulsivity have persisted for at least 6 months to a degree that is maladaptive and inconsistent with development level:
Hyperactivity
(a) Often fidgets with hands or feet or squirms in seat
(b) Often leaves seat in classroom or in other situations in which remaining seated is expected
(c) Often runs about or climbs excessively in situations in which it is inappropriate (in adolescents or adults, may be limited to subjective feelings of restlessness)
(d) Often has difficulty playing or engaging in leisure activities quietly
(e) Is often "on the go" or often acts as if "driven by a motor"
(f) Often talks excessively
Impulsivity
(g) Often blurts out answers before questions have been completed
(h) Often has difficulty awaiting turn
(i) Often interrupts or intrudes on others (e.g., butts into conversations or games)

B. Some hyperactive-impulsive or inattentive symptoms that caused impairment were present before age 7 years.

C. Some impairment form the symptoms is present in two or more setting (e.g., at school (or work) and at home).

D. There must be clear evidence of clinically significant impairment in social, academic, or occupation functioning.

E. The symptoms do not occur exclusively during the course of a Pervasive Developmental Disorder, Schizophrenia, or other Psychotic Disorder and are not better accounted for by another mental disorder (e.g., Mood Disorder, Anxiety Disorder, Dissociative Disorder, or a Personality Disorder).

Attention-Deficit/Hyperactivity Disorder Not Otherwise Specified, DSM-IV-TR 314.9

Attention-Deficit/Hyperactivity Disorder Not Otherwise Specified, according to the DSM-IV-TR is defined as:

This category is for disorders with prominent symptoms of inattention or hyperactivity-impulsivity that do not meet criteria for Attention-Deficit Disorder. Examples include 1. Individuals whose symptoms and impairment meet the criteria for Attention-Deficit/Hyperactivity Disorder, Predominantly Inattentive Type but whose age at onset is 7 years or after 2. Individuals with clinically significant impairment who present with inattention and whose symptom pattern does not meet the full criteria for the disorder but have a behavioral pattern marked by sluggishness, daydreaming, and hypoactivity

Obsessive-Compulsive Disorder, DSM-IV-TR 300.3

Obsessive-Compulsive Disorder, according to the DSM-IV-TR is defined as:

A. Either obsessions or compulsions:

Obsessions as defined as (1), (2), (3), and (4):

(1) Recurrent and persistent thoughts, impulses, or images that are experienced, at some time during the disturbance, as intrusive and inappropriate and that cause marked anxiety or distress (2) The thoughts, impulses, or images are not simply excessive worries about real-life problems (3) The person attempts to ignore or suppress such thoughts, impulses, or images, or to neutralize them with some other thought or action (4) The person recognizes that the obsessional thoughts, impulses, or images are a product of his or her own mind (not imposed from without as in thought insertion)

Compulsions as defined by (1) and (2):

(1) Repetitive behaviors (e.g., hand washing, ordering, checking) or mental acts (e.g., praying, counting, repeating words silently) that the person feels driven to perform in response to an obsession, or according to rules that must be applied rigidly (2) The behaviors or mental acts are aimed at preventing or reducing distress or preventing some dreaded event or situation: however, these behaviors or mental acts either are not connected in a realistic with what they are designed to neutralize or prevent or are clearly excessive B. At some point during the course of the disorder, the person has recognized that the obsessions or compulsions are excessive or unreasonable. Note: This does not apply to children.

C. The obsessions or compulsion cause marked distress, are time consuming (take more than 1 hour a day), or significantly interfere with the person's normal routine, occupational (or academic) functioning, or usual social activities or relationships.

D. If another Axis I Disorder is present, the content of the obsessions or compulsions is not restricted to it.

E. The disturbance is not due to the direct physiological effects of a substance (e.g., a drug of abuse, a medication) or a general medical condition.

Obsessive-Compulsive Personality Disorder, DSM-IV-TR 301.4

Obsessive-Compulsive Personality Disorder, according to the DSM-IV-TR is defined as:

A pervasive pattern of preoccupation with orderliness, perfectionism, and mental and interpersonal control, at the expense of flexibility, openness, and efficiency, beginning by early adulthood and present in a variety of contexts [this disorder, as with all personality disorders, does not begin in early childhood and is therefore not a diagnosis for young children who may otherwise exhibit some of the symptoms associated therewith].

The enduring pattern is not better accounted for as a manifestation or consequence of another mental disorder.

Intermittent Explosive Disorder, DSM-IV-TR 312.34

Intermittent Explosive Disorder, according to the DSM-IV-TR is defined as:

A. Several discrete episodes of failure to resist aggressive impulses that result in serious assaultive acts or destruction of property.

B. The degree of aggressiveness expressed during the episodes is grossly out of proportion to any precipitating psychosocial stressors.

C. The aggressive episodes are not better accounted for another mental disorder and are not due to the direct physiological effects of a substance or a general medical condition.

Impulse Control Disorder Not Otherwise Specified, DSM-IV-TR 312.30

Impulse Control Disorder Not Otherwise Specified, according to the DSM-IV-TR is defined as:

This category is for disorders of impulse control that do not meet the criteria for any specific Impulse Control Disorder or for another mental disorder having features involving impulse control.

Hypomania, DSM-IV-TR

Hypomania, according to the DSM-IV-TR is defined as:

A. A distinct, period of persistently elevated, expansive, or irritable mood, lasting throughout at least 4 days, that is clearly different from the usual nondepressed mood.

B. During the period of mood disturbance, three (or more) of the following symptoms have persisted (four if the mood is only irritable) and have been present to a significant degree:

(1) Inflated self-esteem or grandiosity (2) Decreased need for sleep (e.g., feels rested after only 3 hours of sleep)

(3) More talkative than usual or pressure to keep talking (4) Flight of ideas or subjective experience that thoughts are racing (5) Distractibility (i.e. attention too easily drawn to unimportant or irrelevant external stimuli)

(6) Increase in goal-directed activity (either socially, at work or school, or sexually) or psychomotor agitation (7) Excessive involvement in pleasurable activities that have a high potential of painful consequences (e.g., the person engages in unrestrained buying sprees, sexual indiscretions, or foolish business investments)

C. The episode is associated with an unequivocal change in functioning that is uncharacteristic of the person when not symptomatic D. The disturbance in mood and the change in functioning are observable by others.

E. The episode is not severe enough to cause marked impairment in social or occupational functioning, or to necessitate hospitalization, and there are not psychotic features.

F. The symptoms are not due to the direct physiological effects of a substance (e.g., a drug of abuse, a medication, or other treatment) or a general medical condition (e.g., hyperthyroidism).

The DSM-V, as it is currently proposed for publication later in 2013, no longer presents the following disorders as their own independent classifications: Autistic Disorder, Asperger's Disorder, Retts Disorder and Childhood Disintegrative Disorder. The planned upcoming revision of the DSM-V removes those independent classifications entirely and proposes a single broad classification called Autistic Spectrum Disorder ("ASD"). Patients that may have been formerly diagnosed with Autistic Disorder, Asperger's Disorder, Retts Disorder, Childhood Disintegrative Disorder, or PDD NOS (pervasive developmental disorder, not otherwise specified), may now be reclassified under the broad rubric of ASD or even be left without a diagnosis.

The purpose of proper diagnosis is to guide proper treatment. The reclassification and conflating of the aforementioned disorders as ASD will unfortunately lead psychiatrists to misdiagnose and thus prescribe inappropriate treatment for their patients having some type of pervasive developmental disorder. For example, Risperdal and Abilify, drugs that are currently FDA approved only to treat irritability associated with the original Autistic Disorder, will potentially be misused on patients, whom prior to the proposed DSM-V, were classified as having Asperger's Disorder.

However, an even more dire and widespread consequence of this reclassification is that it will potentially lead psychiatrists away from properly diagnosing and thus properly treating a significant population of PDD patients—potentially millions—who meet a unique set of criteria that make up a novel classification defined below as "P.R.I.C.E." Syndrome. These patients unfortunately may be lost and subsumed under the unduly broad rubric of ASD, if the mental health community is not informed about this new diagnosis. In fact, even under current DSM-IV-TR classifications, patients who meet the criteria for P.R.I.C.E. Syndrome are routinely overlooked or misdiagnosed and thus receive no treatment or the wrong treatment. Until the Applicant's surprising discovery described below, this disorder has not been properly understood nor recognized by the psychiatric community. Thus, patients having this disorder have not been given proper treatment. What is needed is an understanding of this novel diagnosis by the psychiatric community so that psychiatrists can properly identify an appropriate treatment plan for their patients suffering from this disorder. In so doing, potentially millions of currently debilitated people who are misdiagnosed and given the wrong treatment can be put on the appropriate treatment regimen and lead generally healthy and productive lives as a result.

BRIEF SUMMARY OF THE INVENTION

Accordingly, treatments for P.R.I.C.E. Syndrome are provided. In one aspect, the invention comprises administering to a patient having P.R.I.C.E. Syndrome a therapeutically effective amount of an alpha-2 adrenergic agonist in an extended release dosage form. The alpha-2 adrenergic agonist may be, for example, clonidine or guanfacine. In another aspect, the invention comprises administering to a patient having P.R.I.C.E. Syndrome a therapeutically effective amount of inositol in combination with a therapeutically effective amount of extended release clonidine or extended release guanfacine. The inositol may be administered separately (e.g., as a powder mixed with a liquid) or in a combined dosage form (e.g., tablet, capsule or liquid formulation) with the clonidine or guanfacine.

DETAILED DESCRIPTION OF THE INVENTION

The Applicant is a treating psychiatrist in private practice, providing psychotherapy, psychopharmacology and transcranial magnetic stimulation therapy to children, adolescents, adults and couples. The Applicant is also an assistant clinical professor of psychiatry at Weill Cornell Medical College, where he teaches psychiatric diagnostic skills to medical students and psychiatry residents.

The Applicant has recognized a heretofore undiagnosed syndrome consisting of five core requisite psychiatric symptoms, described for the first time herein by the acronym P.R.I.C.E. Syndrome. P.R.I.C.E Syndrome typically has a familial pattern of inheritance, begins in early childhood and persists into adulthood. Since P.R.I.C.E Syndrome is not currently understood or recognized in the field of psychiatry, it is often misdiagnosed as a variety of other DSM-IV-TR diagnoses and is often clearly exacerbated by the recommended pharmacological treatments for those misdiagnoses. It is imperative that the professional and general mental health community take notice of this newly discovered syndrome so as to spare millions of people—especially children and adolescents—the time, expense and deleterious effects of having no diagnosis or being improperly diagnosed and then exposed to harmful treatments which not only fail to improve their condition, but grossly exacerbate it.

Based on experience and insight gained from the Applicant's treatment of certain patients that failed to meet criteria or respond to treatment for known diagnoses, a patient must meet all of the following criteria to be diagnosed as having this newly discovered disorder, P.R.I.C.E. Syndrome:

(1) P. Particularism: exclusive or special preoccupation with a particular, personal, demanding, rigid way of doing things at the expense of flexibility, openness and efficiency and present in a variety of contexts (such as preoccupation with details, rules, lists, order, organization, values, schedules, hoarding, miserliness, rigidity or stubbornness);

(2) R. Reciprocity: deficits in social-emotional reciprocity due to a diminished capacity for sympathy and empathy with abnormal social approach and failure of normal back and forth conversation with reduced sharing of interests, inappropriate emotions, affect and response;

(3) I. Impulsivity: often blurts out answers before questions have been completed and/or often has difficulty waiting for his/her turn and/or often interrupts or intrudes on others (e.g., butts into conversations or games);

(4) C. Concentration: deficits in concentration as evidenced by often having difficulty sustaining attention in tasks or play activities, often does not seem to listen when spoken to directly, is often easily distracted by extraneous stimuli;

(5) E. Emotional Lability: severe, reactive mood swings in response to real or perceived situations where demanded needs are not being met in the environment.

In addition to the foregoing criteria, which form the basis for the P.R.I.C.E. acronym, a patient must also meet the following additional criteria to be properly diagnosed as having P.R.I.C.E. Syndrome:

(6) Symptoms must be consistently present in early childhood;
(7) Symptoms together limit and impair everyday normal functioning;
(8) The disturbance is not better accounted for by another mental disorder (Pervasive Developmental Disorder or Autistic Spectrum Disorder such as Autistic Disorder, Asperger's Disorder, Rett's Disorder, Childhood Disintegrative Disorder, or Schizophrenia or other Psychotic Disorder, or Attention Deficit Hyperactivity Disorder, or Obsessive Compulsive Disorder, or Hypomania in Bipolar Disorder, or Intermittent Explosive Disorder, or an Impulse Control Disorder, or a Personality Disorder. The symptoms are not due to the direct physiological effects of a substance (e.g., a drug of abuse, a medication, or other treatment) or a general medical condition (e.g., hyperthyroidism).

Even if criteria for an exclusionary diagnosis listed above in criterion (8) overlap with some of the P.R.I.C.E. Syndrome criteria, P.R.I.C.E. Syndrome is, by definition, not any of those exclusionary diagnoses. This would be evident to a psychiatrist of ordinary skill who compares the criteria for the various exclusionary diagnoses as defined in the DSM-IV-TR (see above) with the criteria for P.R.I.C.E. Syndrome. However, precisely because there may, in some cases, be overlapping features between P.R.I.C.E. Syndrome and some exclusionary diagnoses listed in criterion (8) for P.R.I.C.E. Syndrome, those exclusionary diagnoses are the ones most often used (or actually, misused) to describe these patients. Those exclusionary diagnoses are not only inaccurate in adequately describing this newly discovered disorder, but result in the misapplication of treatments which are of no benefit and more often exacerbate the targeted diagnosis. It is therefore imperative that P.R.I.C.E. Syndrome not only be recognized as a legitimate diagnosis to help patients and families understand this disorder but to guide proper treatment and avoid exposure to harmful treatments.

The Applicant has surprisingly discovered, that after identifying patients that meet all criteria listed above for P.R.I.C.E. Syndrome, administering to these patients extended release compositions comprising a therapeutically effective amount of an alpha-2 adrenergic agonist, such as extended release clonidine (e.g., marketed as KAPVAY®) or extended release guanfacine (e.g., marketed as INTUNIV®), resulted in marked improvement of all symptoms, virtually without side effects. Both KAPVAY® and INTUNIV® are FDA-approved for treatment of ADHD. However, Applicant has found that stimulants, which are the gold-standard for patients with true ADHD, actually exacerbate symptoms in patients who have P.R.I.C.E. Syndrome. In addition, the "E." criterion for P.R.I.C.E. Syndrome, i.e., emotional lability, suggests a possible mood disorder, which a psychiatrist unfamiliar with P.R.I.C.E. Syndrome may mistake for Bipolar Disorder, for example. A psychiatrist would be led away from prescribing KAPVAY® or INTUNIV® to patients with suspected Bipolar Disorder since it is known that alpha-2 adrenergic agonists could potentially exacerbate emotional lability found in such patients. There have been post-marketing reports in the psychiatric literature correlating the use of alpha-2 adrenergic agonists such as Tenex, INTUNIV® and KAPVAY® with the development or exacerbation of manic symptoms in Bipolar Disorder.

Extended Release Clonidine Formulations

Clonidine is an alpha-adrenergic agonist, known to be effective in various clinical disorders including hypertension; prophylaxis of common migraine headaches; subduing motor tics such as in Tourette's syndrome; and decreasing hyperactivity, impulsivity and over excitability in ADHD, and many other clinical syndromes which involve over arousal.

Clonidine is a 9-carbon, two-ringed imidazoline derivative. As used herein, the term "clonidine" denotes generally one or more of 2,6-dichloro-N-2-imidazolidinylidene benzeneamine, or benzeneamines structurally and functionally related thereto that are described in U.S. Pat. No. 3,454,701, which is incorporated herein by reference in its entirety. With respect to preferred embodiments of the clonidine to be used in extended release dosage forms for the treatment of P.R.I.C.E. Syndrome, the term "clonidine" denotes 2,6-dichloro-N-2-imidazolidinylidene benzeneamine.

Prior to the introduction of KAPVAY® extended release clonidine, the compound clonidine had been typically given in either an oral dose in tablet form three to four times per day or via a transdermal patch. In a short-acting oral formulation, clonidine is almost completely absorbed from the gastrointestinal tract, but it is subject to rapid liver metabolism. The biological half-life ranges from about four to six hours after oral administration of short-acting clonidine, with wide inter-patient variability.

The primary side-effect of short-acting clonidine is sedation, particularly about an hour after the given dose when the patient may become transiently sedated, even falling asleep. Because the half-life of the short-acting dosage form of clonidine is only about four to six hours, there is also the problem of the drug wearing off with some rebound hyperarousal. This can occur in the middle of the night causing insomnia, and even nightmares in some cases. Such side effects have limited the practical usefulness of short-acting clonidine.

The Applicant has found short-acting dosage forms of clonidine to be ineffective in treating P.R.I.C.E. Syndrome. The Applicant has discovered, however, that extended release clonidine, embodied for example in the KAPVAY® formulation, is highly effective in treating patients who meet all criteria for P.R.I.C.E. Syndrome. Extended release clonidine is capable of stable therapeutic effects by maintaining a constant serum level for an extended period in order to avoid the "peak and trough" side effects of transient sedation at peak serum levels and rebound exacerbation of symptoms at trough levels. Embodiments of extended release compositions of clonidine are described in U.S. Pat. No. 5,869,100, which is incorporated herein by reference in its entirety.

The oral dosage units of extended release clonidine may contain one or more compositions such as diluents or fillers which are therapeutically inert and pharmaceutically acceptable and provide bulk. Examples of such diluents or fillers include cornstarch, lactulose, dextrose and the like.

The oral dosage unit of extended release clonidine can be in the form of a tablet or a capsule. Tablets may be prepared or manufactured on any conventional tableting equipment. Where the oral dosage unit is in the form of a capsule, the capsule may be, for example, any standard two-piece gelatin capsule of sufficient size for containing the formulation.

In the preparation of an oral extended release clonidine formulation, clonidine tablets may be ground into a fine powder and mixed with one or more cellulose ethers and one or more diluents or fillers and either tableted or inserted into a gelatin capsule. The amount of clonidine that is included per oral dosage unit may vary widely. The therapeutically effective dose range of about 0.025 mg to about 0.40 mg per unit is preferred for some applications. Twice those amounts of clonidine may be needed per oral dosage unit in a once-a-day formulation. More preferably, the therapeutically effective dose range of clonidine is about 0.10 mg to about 0.40 mg per day. The dose of the oral dosage unit can be exactly specified, however, as required.

The cellulose ethers or mixtures thereof employed as the extended release matrix in the extended release clonidine compositions are ultra-fine, rapidly hydrating formulations having a number average molecular weight of at least 86,000 or a 2% aqueous solution of viscosity of at least 4000 cps and wherein at least 90% by weight of the cellulose ether particles can pass through a 100 mesh screen. The extended release profile of clonidine can be specified by the types or amounts of cellulose ethers used. The composition is thus very adaptable and versatile to each particular use. The oral dosage formulation herein described may provide release periods suitable for the dosing of clonidine twice per day, at twelve hour intervals. It is preferred, however, that the formulation enable once-daily dosing for treatment of P.R.I.C.E. Syndrome.

A functionally effective amount of the cellulose ether composition may be employed in the extended release clonidine formulation. Such an amount is an amount sufficient to extend the release of clonidine for up to twelve hours in some cases, and in other cases for up to about 24 hours (i.e., for once-daily dosing). Such an amount can vary and typically ranges from about 30 to about 70 weight percent, although any functionally effective amount can be employed.

A preferred extended release matrix is hydroxypropyl methylcellulose such as Methocel U.S.A. A preferred Methocel has a hydroxypropoxyl substitution of from about 7 to about 12 weight percent, a methoxyl substitution of from about 28 to about 30 weight percent, a number average molecular weight of about 86,000, a 2% aqueous solution of viscosity of about 4000 cps and 95% by weight can pass through a 100 mesh screen. A preferred Methocel release period is K100M which has a hydroxypropoxyl substitution of from about 7 to about 12 weight percent, a methoxyl substitution of from about 19 to about 24 weight percent, a number average molecular weight of about 246,000, a 2% aqueous solution of viscosity of about 100,000 cps and at least 90% by weight can pass through a 100 mesh screen.

Diluents and fillers, such as cornstarch, lactulose, dextrose and the like, are included in the preparation of extended release clonidine formulation from about 30 to about 70 weight percent based on the weight of the capsule.

Extended Release Guanfacine Formulations

Guanfacine, like clonidine, is an alpha-2 adrenergic agonist, and is described in detail in U.S. Pat. No. 5,854,290, which is incorporated herein by reference in its entirety. Guanfacine (N-(Aminoiminomethyl)-2,6-dichlorobenzeneacetamide; N-amidino-2-(2,6 dichlorophenyl) acetamide) in its short-acting form (Tenex) and extended release form (INTUNIV®) is an FDA approved hypotensive agent. The Applicant has found INTUNIV® to be effective in treating P.R.I.C.E. Syndrome. Other compounds related to guanfacine that may also be effective in treating P.R.I.C.E. Syndrome include other agonists with relative selectivity for the alpha-2A subtype of adrenergic receptor, such as extended release forms of UK14304 and guanabenz, or lofexidine.

Extended released forms of guanfacine, such as the guanfacine hydrochloride, marketed as INTUNIV®, may be made, for example, according to the teachings of U.S. Pat. Nos. 6,287,599 and 6,811,794, which are incorporated herein by reference in their entireties. The preferred therapeutically effective dose range of extended release guanfacine for treating P.R.I.C.E. Syndrome is about 1 mg to about 4 mg per unit.

One extended release guanfacine tablet formulation comprises, in addition of course to the active agent guanfacine (e.g., as a hydrochloride salt), at least one non-pH dependent sustained release agent, and at least one pH-dependent agent that increases the rate of release of the guanfacine from the tablet at a pH in excess of 5.5, such as at least one organic acid that maintains an acidic micro-environment in the tablet. A similar tablet may include clonidine in place of guanfacine as the active agent. In general, the pharmaceutically active agent is present in the composition in an amount of from about 0.1 wt, % to about 70 wt. %, preferably from about 1 wt. % to about 40 wt %.

Non-pH-dependent sustained release agents which may be included in the composition include, but are not limited to, ethylcellulose, cellulose acetate, vinyl acetate/vinyl chloride copolymers, acrylate/methacrylate copolymers, polyethylene oxide, hydroxypropyl methylcellulose, carrageenan, alginic acid and salts thereof, hydroxyethyl cellulose, hydroxypropyl cellulose, karaya gum, acacia gum, tragacanth gum, locust bean gum, guar gum, sodium carboxymethyl cellulose, methyl cellulose, beeswax, carnauba wax, cetyl alcohol, hydrogenated vegetable oils, and stearyl alcohol. In general, the at least one non-pH-dependent sustained release agent is present in the composition in an amount of from about 5 wt. % to about 50 wt. %, preferably from about 10 wt. % to about 30 wt. %. It is to be understood, however, that the scope of the present invention is not to be limited to any particular non-pH-dependent sustained release agents.

pH-dependent agents that increase the rate of release of the at least one pharmaceutically active agent from the tablet at a pH in excess of 5.5 include, but are not limited to, polymers that swell at a pH in excess of 5.5, and enteric agents, and/or agents that increase the solubility of the at least one pharmaceutically active agent at a pH greater than 5.5, by maintaining an acidic microenvironment in the tablet, e.g., an organic acid. The at least one pH-dependent agent is present in the composition in an amount of from about 0.5 wt. % to about 40 wt. %, preferably from about 1 wt. % to about 20 wt. %.

Polymers that swell at a pH in excess of 5.5 include, but are not limited to, acrylic acid copolymers, sodium alginate, carrageenan, alginic acid, pectin, and sodium carboxymethyl cellulose.

Enteric agents include, but are not limited to, cellulose acetate phthalate, hydroxypropyl methylcellulose phthalate, polyvinyl acetate phthalate, methacrylic acid copolymers, cellulose acetate trimellitate, hydroxypropyl methylcellulose acetate, succinate, shellac, and zein.

Agents that increase the solubility of the at least one pharmaceutically active agent at a pH greater than 5.5 include, but are not limited to, organic acids. Such organic acids maintain an acidic microenvironment in the tablet, and include, but are not limited to, citric acid, fumaric acid, tartaric acid, adipic acid, glucono delta-lactone, and malic acid.

The composition of the present invention may further include other materials such as bulking agents, disintegrating agents, anti-adherants and glidants, lubricants, and binding agents.

Bulking agents include, but are not limited to, microcrystalline cellulose (e.g., Avicel®, FMC Corp., Emcocel®, Mendell Inc.), mannitol, xylitol, dicalcium phosphate (e.g., Emcompress, Mendell Inc.) calcium sulfate (e.g., Compactrol, Mendell Inc.) starches, lactose, sucrose (Dipac, Amstar, and Nutab, Ingredient Technology), dextrose (Emdex, Mendell, Inc.), sorbitol, cellulose powder (Elcema, Degussa, and Solka Floc, Mendell, Inc.). The bulking agent may be present in the composition in an amount of from about 5 wt. % to about 90 wt. %, preferably from about 10 wt. % to about 50 wt. %.

Disintegrating agents which may be included in the composition include, but are not limited to, microcrystalline cellulose, starches, crospovidone (e.g., Polyplasdone XL, International Specialty Products), sodium starch glycolate (Explotab, Mendell Inc.), and crosscarmellose sodium (e.g., Ac-Di-Sol, FMC Corp.). The disintegrating agent may be present in the composition in an amount of from about 0.5 wt. % to about 30 wt %, preferably from about 1 wt. % to about 15 wt. %.

Antiadherants and glidants which may be employed in the composition include, but are not limited to, talc, corn starch, silicon dioxide, sodium lauryl sulfate, and metallic stearates. The antiadherant or glidant may be present in the composition in an amount of from about 0.2 wt. % to about 15 wt. %, preferably from about 0.5 wt. % to about 5 wt. %.

Lubricants which may be employed in the composition include, but are not limited to, magnesium stearate, calcium stearate, sodium stearate, stearic acid, sodium stearyl fumarate, hydrogenated cotton seed oil (sterotex), talc, and waxes, including but not limited to, beeswax, carnuba wax, cetyl alcohol, glyceryl stearate, glyceryl palmitate, glyceryl behenate, hydrogenated vegetable oils, and stearyl alcohol. The lubricant may be present in an amount of from about 0.2 wt. % to about 20 wt. %, preferably from about 0.5 wt. % to about 5 wt. %.

Binding agents which may be employed include, but are not limited to, polyvinyl pyrrollidone, starch, methylcellulose, hydroxypropyl methylcellulose, carboxymethyl cellulose, sucrose solution, dextrose solution, acacia, tragacanth and locust bean gum. The binding agent may be present in the composition in an amount of from about 0.2 wt. % to about 10 wt. %, preferably from about 0.5 wt. % to about 5 wt. %.

The compositions of the present invention may be made, for example, by a direct compression method, or by a wet granulation method. In the direct compression method, the pharmaceutically active agent and other ingredients are sieved through a stainless steel screen, such as a 40 mesh steel screen. The sieved materials then are charged to a suitable blender, and blended for 10 minutes with an intensifier bar on for 3 minutes. The blend then is compressed into tablets on a rotary press using appropriate tooling. The compressed tablets may be coated, if desired.

In the wet granulation method, the pharmaceutically active agent and other ingredients are granulated with a granulating fluid (e.g., isopropyl alcohol, ethyl alcohol, and water) in a planetary mixer, high shear mixer, or fluidized bed granulator. Binding agents may be contained in the granulating fluid, or may be in the dry mix. The wet granules are dried in an oven or fluidized bed dryer, and then sieved through a suitable screen to obtain free flowing granules. The resulting granules were blended with a suitable lubricant and glidant, and the lubricated granules are compressed into tablets on a rotary press using appropriate tooling. If desired, a coating can be applied onto the compressed tablets.

Liquid Formulations of Clonidine or Guanfacine

Alternatively, extended release clonidine or guanfacine for the treatment of P.R.I.C.E. Syndrome may be administered orally as a liquid formulation. It is preferred that such a liquid formulation is tasteless and/or odorless because children who have P.R.I.C.E. Syndrome are very particular, do not like swallowing pills and do not respond favorably to medications with strong tastes or smells. It is also preferred that such a liquid formulation is therapeutically effective for treating P.R.I.C.E. Syndrome with once-a-day administration. Extended release liquid of formulations may be prepared, for example, according to the teachings of U.S. Pat. Nos. 8,062,667 and 8,287,903, both of which are incorporated herein by reference. Those two patents purportedly cover Quillivant XR, a recently approved extended release liquid form of Ritalin (methylphenidate hydrochloride) for treatment of ADHD.

Combination Therapy Using Inositol and Clonidine or Guanfacine

In another aspect, the present invention contemplates a combination therapy for treatment of P.R.I.C.E. Syndrome. Such combination therapy would include a therapeutically effective amount of either extended release clonidine or extended release guanfacine in combination with a therapeutically effective amount of inositol. The inositol may be administered separately, along with therapeutic doses of extended release clonidine or extended release guanfacine, as needed. Alternatively, the combination therapy may be in the form of a single extended release formulation comprising inositol and clonidine or guanfacine in, e.g., solid or liquid oral dosage forms.

A preferred form of inositol is that sold in powder form under the name FREEDA®. Therapeutically effective doses of inositol (e.g., in powder form) for patients with P.R.I.C.E. Syndrome may range from 4,500 mg to 18,000 mg per day (e.g., in once or twice daily administrations). If taken in powder form, inositol is typically dissolved in a drink. It is contemplated that the inositol can also be administered in solid oral dosage forms too, such as in tablets or capsules.

Alternatively, as mentioned above, therapeutically effective amounts of inositol and clonidine or guanfacine may be combined in a single oral formulation. In one aspect, this formulation may be in a solid oral dosage form, such as in a tablet or capsule. It is also contemplated that this oral formulation may be in a liquid formulation—preferably one that is tasteless and odorless. The oral formulation may be used for twice daily administration, but more preferably once daily administration. As described in examples below, it has been found that inositol nicely complements KAPVAY® or INTUNIV® in effectively treating the symptoms of P.R.I.C.E. Syndrome.

Examples of Treatment for P.R.I.C.E. Syndrome

The following examples demonstrate the current, inadequate state of psychiatric diagnosis using DSM-IV-TR for people who meet the criteria of P.R.I.C.E. Syndrome and how adverse reactions to FDA approved treatments for the proposed alternative diagnoses help disprove the validity of applying those diagnoses in cases of P.R.I.C.E. Syndrome. Once the diagnosis of P.R.I.C.E. Syndrome is properly applied, other ineffective and/or harmful treatments can be tapered and discontinued while INTUNIV® or KAPVAY® can be initiated and titrated to an effective dose, augmented if necessary, or co-administered, e.g., in a combined therapeutic formulation, with inositol. Upon discontinuation of either INTUNIV® or KAPVAY®, or inositol, the patient with P.R.I.C.E. Syndrome reverts to his or her baseline symptomatology. Once the effective treatment regimen is resumed, the symptoms abate as before.

The present invention is further explained by the following examples which should not be construed by way of limiting the scope of the present invention.

EXAMPLE 1

Diagnosis of P.R.I.C.E. Syndrome and Treatment of the Same Using KAPVAY®

A patient was initially diagnosed ten years ago with alleged Attention Deficit Hyperactivity (ADHD) at age six by his original psychiatrist due to difficulties with concentration and impulsivity which impaired his social and academic functioning, following normal labs and physical examination. The patient's mother's pregnancy and delivery were unremarkable. The patient met normal developmental, motor milestones. The patient was tried on many psychostimulant medications, which are the gold standard for treatment of ADHD. Medications in this class include: Adderall/XR, Focalin/XR, Dexedrine, Vyvanse, Ritalin/LA/ER, Metadate ER/CD, Concerta and Daytrana. Despite adequate dosing and duration of trials of several such psychostimulants, the patient manifested an increase in agitation and impulsivity without improving concentration in school on these medications, instead of the calming effect stimulant medication is expected to exert in ADHD patients.

After the failure of these psychostimulants to improve the patient's symptoms, the psychiatrist separately tried Strattera, Wellbutrin, Provigil and Nuvigil to treat ADHD, all of which similarly increased agitation and impulsivity in this patient. In addition, many of these medications produced the typical side effects of decreased appetite, abdominal pain, nausea and difficulty sleeping at night. These side effects limited the drugs' usefulness, particularly in these patients who are particular, rigid and inflexible when it comes to accepting change—in this case, the side effects themselves.

Next, the psychiatrist attempted to address the patient's impulsivity with three-times-daily, short-acting guanfacine (Tenex), followed by short-acting clonidine, followed by propranolol, which were not effective because they were too sedative. Also, the thrice-daily dosing of these drugs left peaks and troughs in the patient's symptoms and difficulty with compliance during the school day.

Due to a failure of ADHD treatments, the psychiatrist concluded that this patient did not have ADHD. The psychiatrist thus changed his treatment approach to address alleged Obsessive Compulsive Disorder (OCD) symptoms that the patient manifested, such as rigidity and preoccupation with his daily routine which often distracted the patient and caused him to become impulsive and irritated when he did not get his way. He was tried on many serotonergic medications (selective serotonin re-uptake inhibitors ("SSRI's") and serotonin and norepinephrine reuptake inhibitors ("SNRIs"), which are the gold standard for treatment of OCD. Medications in this class include Celexa, Lexapro, Prozac, Luvox/CR, Paxil/CR, Zoloft, Pristiq, Effexor/XR, Cymbalta and Remeron. Despite adequate dosing and duration of trials of several of these SSRI/SNRI medications, the patient manifested an increase in agitation and impulsivity without improvement in concentration in school on these medications, instead of the calming effect SSRI/SNRI medications were expected to exert in OCD patients.

The psychiatrist next presumed that the activation of agitation and impulsivity in the patient on psychostimulants and serotonergic medications suggested an underlying mood disorder such as pediatric Bipolar. In addition, the psychiatrist determined that the observed impulsivity must represent a pediatric manifestation of hypomania, despite the absence of other hypomanic symptoms found in DSM-IV-TR. By convention, psychiatrists refer to this phenomenon as Bipolar III or hypomania induced by medication which predicts and unmasks the development of spontaneous mood swings of genuine Bipolar to come for the patient later in life.

With the patient diagnosed (or rather, misdiagnosed) as having pediatric Bipolar, the psychiatrist tried a series of mood stabilizers to address the patient's impulsivity, such as Lithium, Depakote, Topamax, Trileptal, Tegretol, and Lamictal—all of which proved ineffective and resulted in the side effects of worsening the patient's concentration. Given the lack of efficacy of the mood stabilizers and the lack of clear evidence for Bipolar Disorder in this patient, the psychiatrist turned his attention to a possible Pervasive Developmental Disorder such as Asperger's Disorder, since the patient never exhibited the speech delay required to qualify for a diagnosis of Autistic Disorder. Yet this patient did not meet all criteria for Asperger's Disorder either, except that he lacked normal social skills. Nevertheless, the psychiatrist tried a series of atypical antipsychotics, including Zyprexa, Geodon, Seroquel as well as two FDA approved drugs for treatment of irritability in Autistic Disorder, Abilify and Risperdal. These medications caused the patient severe sedation, impaired his concentration further and caused an increase in both appetite and weight. These side effects caused the patient further irritation.

After this series of misdiagnoses and treatment regimens that exacerbated the patient's condition, the patient was sixteen years old when he first met with the Applicant for a psychiatric evaluation. The Applicant determined that the patient was worse on his then-current medication regimen than he was without it. He had been taking Daytrana, which appeared to worsen his agitation without helping his concentration. He had been taking Lexapro which also appeared to be worsening his agitation without helping his rigidity. He had been taking Depakote and Lamictal which was making him tired, was not helping his agitation and impaired his concentration. His diagnosis was completely unclear until the Applicant evaluated him for the diagnostic criteria for P.R.I.C.E. Syndrome. It was found that every one of the criteria for P.R.I.C.E. Syndrome were present for this patient.

The Applicant tapered and discontinued the aforementioned medications in the patient. The Applicant then titrated up KAPVAY® as follows: 0.1 mg at bedtime for a week; next, 0.1 mg twice a day for a week; next, 0.1 mg in the morning and 0.2 mg at night for one week; and finally 0.2 mg twice a day going forward. Every symptom of P.R.I.C.E. Syndrome in this patient was dramatically improved without side effects. The patient still had mild, residual particular tendencies of rigidity with rules and schedule for which the Applicant added Inositol powder (sold under the name FREEDA®) 2 and ½ teaspoons (9000 mg) twice a day, which was well tolerated. Within one month, the patient appeared as a normal teenager. He went off his medications while on vacation and all of his symptoms returned. He then resumed his regimen and became normal again. Thus, a patient who had been misdiagnosed and consequently suffered for so many years, was finally able to live as basically a normal teenager because he was given the proper, novel diagnosis of P.R.I.C.E. Syndrome, and was accordingly put on the appropriate therapy which the Applicant discovered is effective for treating such patients.

EXAMPLE 2

Diagnosis of P.R.I.C.E. Syndrome and Treatment of the Same Using INTUNIV®

The Applicant evaluated a sixteen year old patient who had a history of all the symptoms of P.R.I.C.E. Syndrome, the clinical significance of which had not been previously appreciated nor diagnosed. The patient had been misdiagnosed as having OCD four years ago and was given Prozac and Zoloft. These drugs did not alleviate the particularism and caused the patient to become "wild" and unable to sleep. Risperdal was added to the patient's therapeutic regimen for mood swings associated with possible Bipolar Disorder, misdiagnosed due to the activation on the SSRI's and to help control agitation associated with possible Asperger's Disorder. However, the patient did not meet criteria for Asperger's Disorder other than lacking social skills. Risperdal was then discontinued due to sedation and weight gain. The patient was switched to Abilify which also caused sedation and tremor without improvement in concentration.

By the time the patient met with the Applicant for an initial psychiatric evaluation, he was worse on his then-current medication regimen than he was without it. He had been taking Zoloft and Abilify, as well as Melatonin to help him sleep. His diagnosis was completely unclear until the Applicant evaluated him for the diagnostic criteria for P.R.I.C.E. Syndrome. It was found that every one of the criteria for P.R.I.C.E. Syndrome were present for this patient.

The Applicant tapered and discontinued the patient's then-current medications. The Applicant then titrated up INTUNIV® 1 mg at bedtime, increasing by an additional 1 mg at bedtime every week as necessary to achieve symptom control, up to a maximum of 4 mg.

This patient ultimately did very well on INTUNIV® 2 mg at bedtime, which also helped him sleep at night. The addition of Inositol 9000 mg twice day for "getting stuck" on certain topics in conversation was found to be therapeutically beneficial. On this new treatment, every symptom of P.R.I.C.E. Syndrome in this patient was dramatically improved without side effects. It was found that when this patient went off his medications, e.g., on holidays, all P.R.I.C.E. Syndrome symptoms returned. When he resumed his treatment regimen, he was normal again.

EXAMPLE 3

Diagnosis of P.R.I.C.E. Syndrome and Treatment of the Same Using INTUNIV®

A six year old patient, who happens to be the Applicant's son, meets all criteria for P.R.I.C.E. Syndrome. This patient had been evaluated by other specialists, who had determined that he had some type of pervasive developmental disorder (PDD-NOS), for which there was no known treatment. This patient's condition rendered him unfit to be in a mainstream school with children who have normal social skills.

When the Applicant discovered the novel diagnosis of P.R.I.C.E. Syndrome and determined that his son met all criteria for that condition, the Applicant initiated treatment using 1 mg of INTUNIV® once per day. The results were nothing short of miraculous. All symptoms of P.R.I.C.E. Syndrome were significantly improved and without side effects. The Applicant, as both a psychiatrist and father who lives with this patient can attest to the effectiveness and tolerability of this treatment. The Applicant noted that his son would completely relapse when off drug but become "normal" again upon resuming treatment. For example, the patient's P.R.I.C.E. Syndrome symptoms returned when the INTUNIV® was withheld on weekends, but would abate upon resuming administration of the drug during the school week.

If the Applicant had simply accepted that his son had some form of PDD-NOS, the Applicant could have accepted the conventional wisdom that there is no treatment for his son. Alternatively, the Applicant could have tried to treat certain symptoms of his son's using medications that were known for certain PDD's specified in the DSM-IV-TR. In other words, Applicant could have easily prescribed numerous improper medications carrying a host of side effects and adverse reactions due to misdiagnosis with conditions such as Autistic Disorder, Asperger's Disorder, PDD-NOS, Autistic Spectrum Disorder, ADHD (for which stimulants are the gold standard), OCD, Bipolar Disorder, Intermittent Explosive Disorder or Impulse Control Disorder. This is precisely what happened to the patients described in Examples 1 and 2 above, before they were diagnosed as having P.R.I.C.E. Syndrome.

INTUNIV® has made the difference for the Applicant's son between the need for expensive tax payer or private resources exceeding $50,000 a year in special education services and a normal, mainstream, elementary school education, which is to the patient's maximal benefit. He is now immersed in a classroom of children with normal social skills and is thriving in that environment.

The patients in the Examples above, in addition to others the Applicant has seen, were initially evaluated and (mis)diagnosed by top practitioners in the mental health field, using the most sophisticated diagnostics that are known in psychiatry. These misdiagnoses are not the fault of the psychiatrists, since P.R.I.C.E. Syndrome and the treatment for it have not been heretofore known in the art. If, however, P.R.I.C.E. Syndrome and its treatment, as described herein, does not become well known and utilized by the mental health community, these diagnostic and treatment dilemmas will continue.

Unfortunately, the most recent iteration of the DSM, i.e., the DSM-V, due out later in 2013, only compounds the diagnostic dilemma by obliterating all sub-classification of PDDs and re-naming them all Autistic Spectrum Disorder or ASD. The DSM-V proposed definition of ASD is as follows:

A. Persistent deficits in social communication and social interaction across contexts, not accounted for by general developmental delays, and manifest by all 3 of the following:
   1. Deficits in social-emotional reciprocity: ranging from abnormal social approach and failure of normal back and forth conversation through reduced sharing of interests, emotions, and affects and response to total lack of initiation of social interaction.
   2. Deficits in nonverbal communicative behaviors used for social interaction: ranging from poorly integrated verbal and nonverbal communication, through abnormalities in eye contact and body language, or deficits in understanding and use of nonverbal communication, to total lack of facial expression or gestures.
   3. Deficits in developing and maintaining relationships appropriate to developmental level (beyond those of caregivers); ranging from difficulties to adjusting behavior to suit different social contexts through difficulties in sharing imaginative play and in making friends to an apparent absence of interest in people.

B. Restricted, repetitive patterns of behavior, interests, or activities as manifested by at least two of the following:

1. Stereotyped or repetitive speech, motor movements, or use of objects (such as simple motor stereotypies, echolalia, repetitive use of objects, or idiosyncratic phrases).
2. Excessive adherence to routines, ritualized patterns of verbal or nonverbal behavior, or excessive resistance to change (such as motoric rituals, insistence on same route or food, repetitive questioning or extreme distress at small changes).
3. Highly restricted, fixated interests that are abnormal in intensity or focus (such as strong attachment to or preoccupation with unusual objects, excessively circumscribed or perseverative interests).
4. Hyper- or hypo-reactivity to sensory input or unusual interest in sensory aspects of environment (such as apparent indifference to pain/heat/cold, adverse response to specific sounds or textures, excessive smelling or touching of objects, fascination with lights or spinning objects).

C. Symptoms must be present in early childhood (but may not become fully manifest until social demands exceed limited capacities).

D. Symptoms together limit and impair everyday functioning.

Notably, unlike ASD under DSM-V, the required P.R.I.C.E. Syndrome criteria includes "I.", i.e., impulsivity, "C.", i.e., concentration deficits and "E.", i.e., emotional lability (severe, reactive mood swings in response to real or perceived situations where demanded needs are not being met in the environment). A patient diagnosed with DSM-V ASD who does not exhibit these aforementioned symptoms, will not respond to treatment with INTUNIV® or KAPVAY®.

If all PDDs are conflated under the umbrella of ASD as proposed in the DSM-V, then P.R.I.C.E. Syndrome will unfortunately likely continue to be misdiagnosed because patients who actually have that disorder, may get lost and subsumed under the broad and unhelpful rubric of ASD. Accordingly, potentially millions of children, adolescents and adults suffering from a readily treatable syndrome, P.R.I.C.E. Syndrome, may be misdiagnosed as having ASD under DSM-V, and will not be guided to receive proper treatment, e.g., with INTUNIV® or KAPVAY®.

INTUNIV® and KAPVAY® are currently only FDA approved for the treatment of ADHD. These medications have not been proven effective for the core symptoms of Asperger's Disorder or classic Autistic Disorder. In addition, according to the DSM-IV-TR, ADHD cannot be diagnosed in the context of a Pervasive Developmental Disorder which currently precludes using INTUNIV® and KAPVAY® on-label in this population. If, according to the proposed DSM-V, ADHD may be diagnosed in the context of ASD, INTUNIV® and KAPVAY® may still only address symptom clusters "I." and "C." and not the five full features of P.R.I.C.E. Syndrome. The Applicant estimates that P.R.I.C.E. Syndrome is, by far, the most prevalent of all Pervasive Developmental Disorders/Autistic Spectrum Disorders—yet has gone unrecognized by the mental health community and thus untreated.

In the Applicant's own practice, in which the Applicant sees approximately 400 new patients per year, only about one of these new patients per year has classic DSM-IV-TR Autism and only about one of these new patients per month has Asperger's Disorder. But now that the Applicant understands and appreciates the criteria for P.R.I.C.E. Syndrome, the Applicant estimates that he sees one such new patient per week. Current estimates of ASD are 1 in 50 children, which makes P.R.I.C.E. Syndrome a condition affecting millions of patients. These facts demonstrate the urgent public health need for the mental health community to understand P.R.I.C.E. Syndrome as a novel, necessary diagnostic construct and a vital vehicle to guide proper treatment with, e.g., INTUNIV® or KAPVAY®. These drugs work exceptionally well to alleviate this disorder with minimal side effects. The addition of inositol is also effective in addressing residual particularism. The Applicant's invention provides a readily available, safe and comparatively low-cost means to enable P.R.I.C.E. Syndrome sufferers to lead normal lives. Widespread implementation of this invention would address the exorbitant educational, medical and societal costs caused by this condition.

While the invention has been described in detail and with reference to specific examples thereof, it will be apparent to one skilled in the art that various changes and modifications can be made therein without departing from the spirit and scope thereof.

What is claimed is:

1. A method for treating a patient having Pervasive Developmental Disorder Not Otherwise Specified as defined in the Diagnostic and Statistical Manual of Mental Disorders IV-TR, comprising administering to the patient a therapeutically effective amount of an extended release dosage form of an alpha-2 adrenergic agonist selected from the group consisting of clonidine and guanfacine, in combination with a therapeutically effective amount of inositol.

2. The method of claim 1 wherein the therapeutically effective amount of clonidine is from about 0.10 mg to about 0.40 mg per day and the therapeutically effective amount of guanfacine is from about 1 mg to about 4 mg per day.

3. The method of claim 1 wherein the extended release dosage form is a once-daily dosage form.

4. The method of claim 1 wherein the extended release dosage form is an oral solid dosage form.

5. The method of claim 1 wherein the extended release dosage form is a liquid dosage form.

6. The method of claim 5 wherein the liquid dosage form is tasteless and odorless.

7. The method of claim 1 wherein the therapeutically effective amount of inositol is from about 9,000 mg to about 18,000 mg per day.

8. The method of claim 1, wherein the patient has a symptom of Impulsivity.

9. The method of claim 8, wherein the symptom of Impulsivity is improved by the method.

10. The method of claim 1, wherein the patient has a symptom of Concentration.

11. The method of claim 10, wherein the symptom of Concentration is improved by the method.

12. The method of claim 1, wherein the patient has a symptom of Emotional Lability.

13. The method of claim 12, wherein the symptom of Emotional Lability is improved by the method.

14. The method of claim 1, wherein the patient has symptoms of Particularism, Reciprocity, Impulsivity, Concentration and Emotional Lability, and wherein the symptoms of Particularism, Reciprocity, Impulsivity, Concentration and Emotional Lability are improved by the method.

15. A method for treating a patient having Pervasive Developmental Disorder Not Otherwise Specified as defined in the Diagnostic and Statistical Manual of Mental Disorders IV-TR and a symptom of Emotional Lability, comprising administering to the patient a therapeutically effective amount of 9,000 mg to about 18,000 mg per day of inositol in combination with either from about 0.10 mg to about 0.40 mg of clonidine in an extended release dosage form or from about 1 mg to about 4 mg of guanfacine in an extended release dosage form.

16. The method of claim 15, wherein the symptom of Emotional Lability is improved by the method.

17. The method of claim 1, wherein the patient has symptoms of Particularism and Reciprocity and wherein the symptoms of Particularism and Reciprocity are improved by the method.

18. The method of claim 17, wherein the therapeutically effective amount of inositol is from about 9,000 mg to about 18,000 mg per day.

* * * * *